(12) United States Patent
Ng et al.

(10) Patent No.: US 6,533,920 B2
(45) Date of Patent: Mar. 18, 2003

(54) DEVICE FOR DETECTING AN END POINT OF ELECTRO-PLATING AND METHOD THEREOF

(75) Inventors: Joo Khim Joachim Ng, Singapore (SG); Hock Choon Tan, Singapore (SG)

(73) Assignee: Hewlett-Packard Company, Palo Alto, CA (US)

( * ) Notice: Subject to any disclaimer, the term of this patent is extended or adjusted under 35 U.S.C. 154(b) by 76 days.

(21) Appl. No.: 09/757,129

(22) Filed: Jan. 8, 2001

(65) Prior Publication Data
US 2002/0088721 A1 Jul. 11, 2002

(51) Int. Cl.$^7$ .................. G01N 27/26; C25D 21/12
(52) U.S. Cl. .................. 205/775; 205/81; 205/82; 205/83; 205/791; 205/794; 204/400; 204/434
(58) Field of Search .................. 205/81, 82, 83, 205/775, 791, 794; 204/434, 400

(56) References Cited

U.S. PATENT DOCUMENTS

| | | | |
|---|---|---|---|
| 4,773,971 A | | 9/1988 | Lam et al. |
| 5,338,390 A | * | 8/1994 | Barbee et al. .............. 204/434 |
| 5,685,074 A | | 11/1997 | Pan et al. |
| 6,231,743 B1 | * | 5/2001 | Etherington ................. 205/81 |
| 6,350,361 B1 | * | 2/2002 | Sexton et al. ............... 205/641 |

* cited by examiner

*Primary Examiner*—Robert J. Warden, Sr.
*Assistant Examiner*—Kaj K. Olsen

(57) ABSTRACT

A device for detecting an end point of electro-plating comprises a mandrel having a substrate and a patterned conductive layer with a main conductive area and an insulated conductive area on the substrate, an insulation region interposed between the main conductive area and the insulated conductive area, and a sensor electrically connected to the insulated conductive area for detecting a signal which indicates the end point of electro-plating.

18 Claims, 4 Drawing Sheets

DEVICE FOR DETECTING AN END POINT OF ELECTRO-PLATING AND METHOD THEREOF

BACKGROUND OF THE INVENTION

The invention relates to a device for and a method of detecting an end point of electro-plating, which is necessary, for instance, for producing orifice sheets.

Orifice sheets as known for instance from inkjet printheads are usually fabricated by one of the following two different methods, which are generally known. The first method is a mechanical method and the second method is an epitaxial growth method.

In the mechanical method, as described in U.S. Pat. No. 5,685,074, a thin sheet or tape is fabricated by any common sheet or tape fabrication process. This thin sheet or tape is put onto an anvil and a punching device punches bores at desired positions through the thin sheet or tape. Afterwards, the thin sheet or tape comprising bores at desired positions is cut to the desired form and size, yielding the orifice sheets. Another way of mechanically producing orifice sheets is to cut the thin sheet or tape first, yielding small formed sheets. Then, these small formed sheets are put onto an anvil and a punching device punches bores at desired positions through the small formed sheets, yielding the orifice sheets. This mechanical method bears the disadvantage, that the position of the bores in the orifice sheet is not reproducible to each other as well as to the borders of the orifice sheet. Additionally, the compound as well as the thickness of different thin sheets or tapes can easily vary between different cycles of production during any common sheet or tape fabrication process or between different common sheet or tape fabrication processes.

In the epitaxial growth method usually a vapor deposition process, e.g., a chemical vapor deposition (CVD) process, a plasma enhanced chemical vapor deposition (PECVD) process, a molecular beam epitaxy (MBE) process, and the like, or an electro-plating process is employed for fabricating an orifice sheet. Desired material is grown up epitaxially on a substrate in both different production processes, thereby forming an orifice sheet layer on the substrate, which is finally removed from the substrate for yielding the orifice sheet. The above mentioned vapor deposition processes can make use of masks for producing bores during growing up the orifice sheet. The use of a mask, however, has the disadvantage, that the diameters as well as the position of the bores are not exactly controllable.

The best results during producing orifice sheets according to the state of the art are delivered by an electro-plating process. This process usually makes use of a mandrel having a substrate and a thin conductive layer on the substrate. Such a mandrel is known from U.S. Pat. No. 4,773,971. There is further disclosed, that the conductive layer is etched to form a mold for the orifice sheets, which should be manufactured. This mold is electro-plated with a desired orifice sheet material. The final orifice sheet is removed from the mold after electro-plating. The electro-plating process makes use of a constant current or a constant voltage, respectively, and an adjusted electro-plating time to achieve the desired thickness of the final orifice sheet and to achieve the desired bore size or bore diameter, respectively. Due to the variability of the electro-plating rates between different cycles of electro-plating as well as between different electro-plating apparatus, time consuming and costly pre-control electro-plating runs are required to estimate the electro-plating time, which is required for each electro-plating apparatus at the beginning of each cycle of electro-plating.

SUMMARY OF THE INVENTION

One main aspect of the invention is to provide a possibility to detect the desired end point of electro-plating, which is universally applicable, i.e., independent from variations of the electro-plating rates between different cycles of electro-plating as well as between different electro-plating apparatus.

A device for detecting an end point of electro-plating and a method thereof according to the independent claims of the invention avoids time consuming and costly pre-control electro-plating runs.

A device for detecting an end point of electro-plating according to the invention comprises a mandrel having a substrate and a patterned conductive layer on the substrate, an insulation region, and a sensor. The patterned conductive layer comprises a main conductive area and an insulated conductive area. The insulated conductive area is electrically insulated from the main conductive area by the interposed insulation region. The sensor is electrically connected to the insulated conductive area for detecting a signal which indicates the end point of electro-plating.

A method of detecting an end point of electro-plating according to the invention provides above all a mandrel having a conductive layer on a substrate. Then, an insulation region is provided interposed on the substrate between two areas of the conductive layer, which yields a main conductive area and an insulated conductive area. Afterwards, a sensor is electrically connected to the insulated conductive area. Subsequently, a layer of conductive material is electro-plated on the main conductive area to cross the insulation region. Finally, a signal is detected by the sensor when the electro-plated layer of conductive material contacts the insulated conductive area, i.e. an electrical shortcut occurs between the main conductive area and the insulated conductive area, which indicates the end point of electro-plating.

One advantage of the invention over the prior art is, that time can be saved in every production cycle by eliminating the need of pre-control electro-plating runs. Another advantage of the invention is that the thickness of the electro-plated conductive material, the bore shape, the bore size and the bore diameter can be precisely adjusted, either singly or in any desired combination with one another, by means of patterning the insulation region with a desired depth, width and shape.

The above and other objects, features and advantages of the present invention will become apparent from the following description and the appended claims, taken in conjunction with the accompanying drawings in which like parts or elements are denoted by like reference numbers.

DETAILED DESCRIPTION OF PREFERRED EMBODIMENTS OF THE INVENTION

As already mentioned above, one advantage of the invention is that the thickness of the electro-plated conductive material, the bore shape, the bore size and the bore diameter can be precisely adjusted, either singly or in any desired combination with one another. For instance, this is reachable by the following procedure: First, a conductive layer is patterned on a substrate for yielding a main conductive area and an insulated conductive area. Then, an insulation region is formed interposed on the substrate between the main conductive area and the insulated conductive area, and the main conductive area without the insulated conductive area is charged. The insulation region is preferably an insulation trench which is just as deep as the conductive layer thick, and which extends to the substrate. Afterwards, a layer of conductive material is electro-plated on the charged main conductive area such that additionally electro-plated conductive material extends out into the insulation trench as a sort of meniscus, the radius of which increases with increasing electro-plating time. Continuing electro-plating increases the size of the meniscus such that the meniscus finally extends to and contacts the insulated conductive area. At this point, an electrical contact between the main conductive area and the insulated conductive area is established through the electro-plated layer of conductive material. Finally, a sensor detects for stopping the electro-plating process the point of time, when the electro-plated layer of conductive material establishes the electrical contact between the charged main conductive area and the insulated conductive area.

The depth of the insulation trench relative to the conductive layer and its width define the duration of electro-plating conductive material onto the main conductive area and across the insulation trench until an electrical contact between the charged main conductive area and the insulated conductive area is established. Therefore, the duration of electro-plating is controlled independently from the conditions in different electro-plating apparatus by forming the shape of the insulation region using techniques like epitaxial growth and chemical etch in a desired manner.

Preferred embodiments of the invention will now be described with reference to the attached drawings in which like parts or elements are denoted by like reference numbers.

Figure 1:
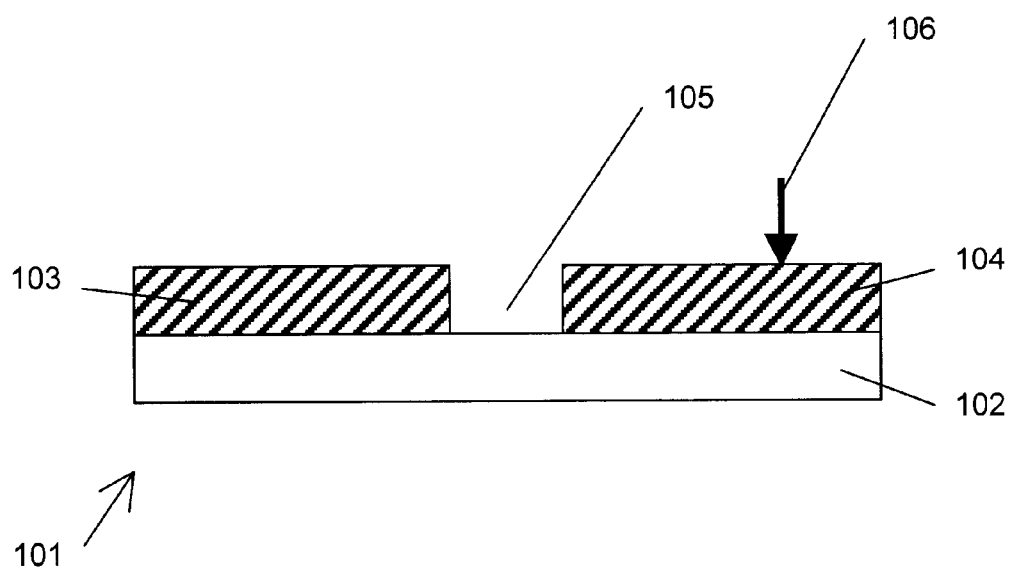
FIG. 1 shows a schematic side view of a first embodiment of the invention.

FIG. 1 shows a schematic side view of a mandrel 101 of a first embodiment of the invention. The mandrel 101 comprises a substrate 102 and a patterned conductive layer. The patterned conductive layer is partially shown with a main conductive area 103 and an electrically insulated conductive area 104. An insulation trench 105 is used as insulation region and separates the insulated conductive area 104 and the main conductive area 103. The insulation trench 105 should be formed around the insulated conductive area 104 such that the insulated conductive area 104 is completely insulated against the main conductive area 103. Electrically connected to the insulated conductive area 104 is a sensor 106 which can detect charging of the insulated conductive area 104.

Silicon is a preferred material for the substrate 102. This is due to the fact, that silicon is easily available and easy to machine. It is also possible to use other semiconductors as well as insulators for the substrate 102, for instance silicon-dioxide glass. The main conductive area 103 as well as the insulated conductive area 104 comprise in this embodiment of the invention a chromium steel alloy. It is preferred that the chromium steel alloy for the main conductive area 103 and for the insulated conductive area 104 comprises between 16% and 18% chromium.

Figure 2:
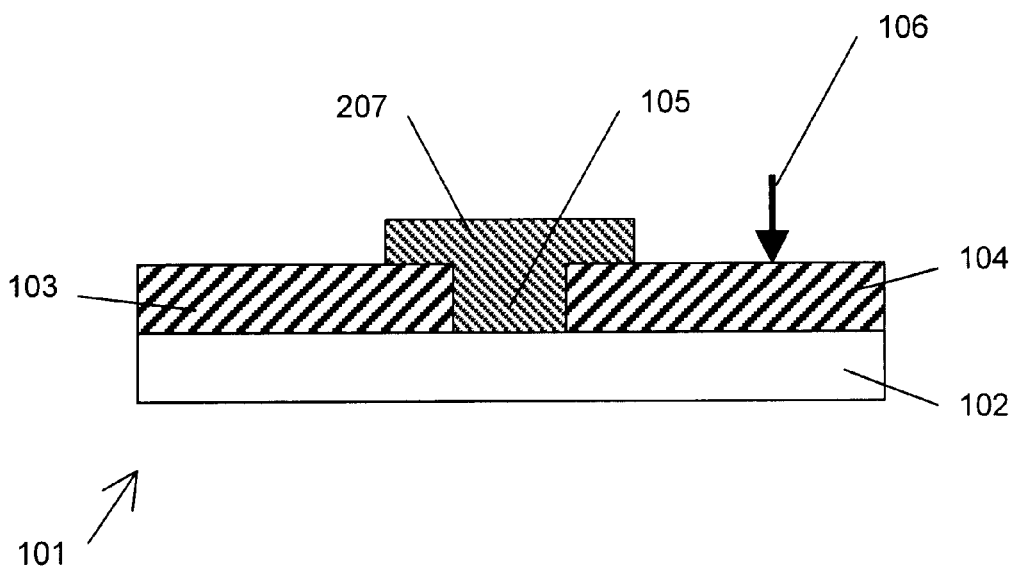
FIG. 2 shows a schematic side view of a second embodiment of the invention.

FIG. 2 shows a schematic side view of a mandrel 101 of a second embodiment of the invention. The mandrel 101 comprises mainly the same elements as in FIG. 1. The insulation trench 105 is overfilled with insulating material such as silicon carbide and the like. The overfilled insulating material can be patterned and etched for yielding an insulation ridge 207 with a desired shape. The cross section of the insulation ridge 207 can be viewed as a plug which is located in the insulation trench 105. Following possible patterning and/or etching, the surface of the plug-like insulation ridge 207 can be flush with the surfaces of the main conductive area 103 as well as the insulated conductive area 104 or can extend out above said surfaces in the case that the insulating material still overfills the insulation trench 105. The insulation ridge 207 can then have a curved, i.e., meniscus-like, shape, the cross section of which has a generally mushroom-shape. Alternatively, the insulation ridge 207 can have a cornered shape, so that its cross section has a generally T-shape, as shown in FIG. 2.

FIGS. 3 to 6 show four snapshots of a method according to the invention by means of a mandrel 101 of the second embodiment of the invention, wherein each snapshot shows the mandrel 101 in a different mode. It is important to mention that the method described by means of the four snapshots is also feasible by means of the mandrel 101 of the first embodiment of the invention or of a third embodiment of the invention, which is described with respect to FIGS. 7 and 8.

Figure 3:
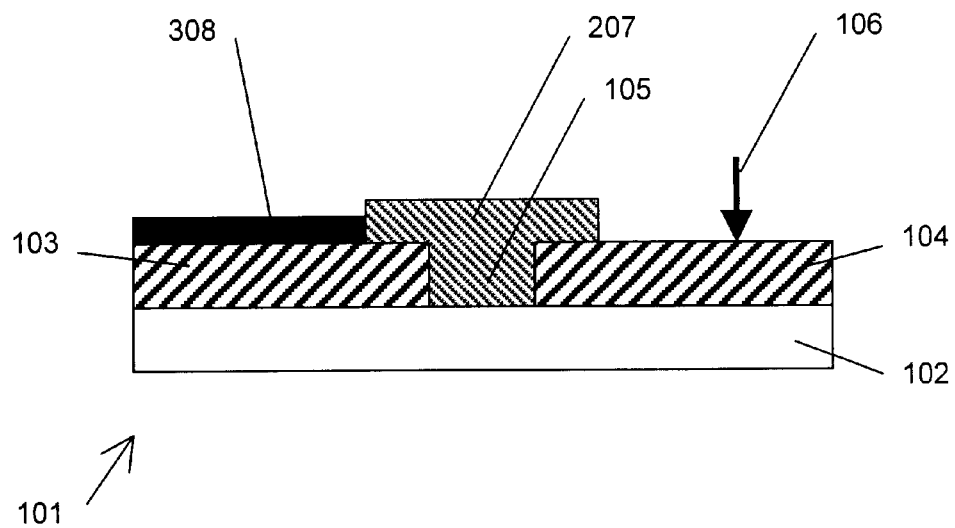
FIG. 3 shows a schematic side view of the second embodiment of the invention in a first mode.

In FIG. 3 a schematic side view of the mandrel 101 of the second embodiment of the invention is shown in a first mode. Similar to FIG. 2, the mandrel 101 comprises the same elements as in FIG. 1. As already mentioned is the sensor 106 designated for detecting charging of the insulated conductive area 104. The insulated conductive area 104 remains uncharged in this state. The main conductive area 103 was charged and conductive material was electro-plated onto the charged main conductive area 103 yielding a first mode layer of conductive material 308. The electro-plated conductive material is grown up onto the main conductive area 103 as a homogeneous layer. The conductive material is not electro-plated at localized positions on the main conductive area 103.

Figure 4:
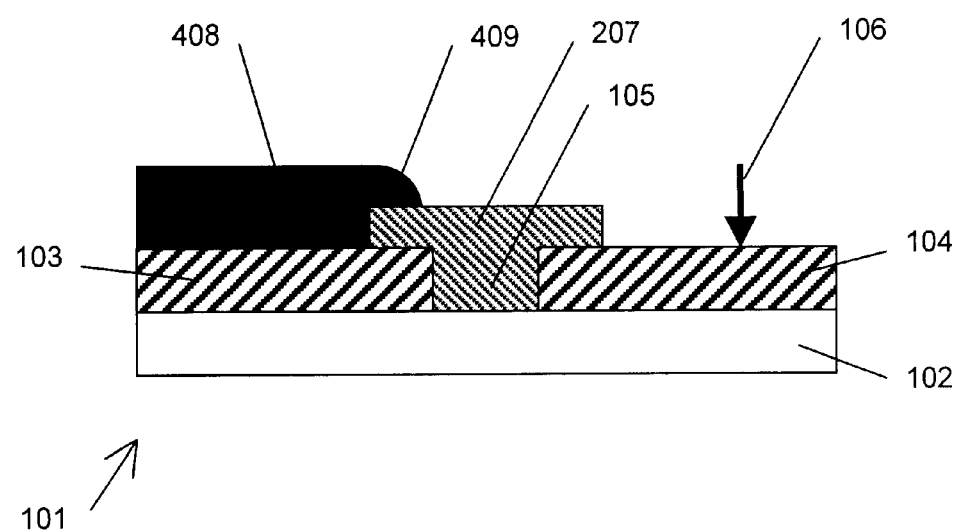
FIG. 4 shows a schematic side view of the second embodiment of the invention in a second mode.

After further electro-plating the mandrel 101 with conductive material, the first mode layer of conductive material 308 is proceeded to a second mode layer of conductive material 408, as shown in FIG. 4. Conductive material was electro-plated on the first layer of conductive material 308, which is charged at the same time, as conductive material was electro-plated on the charged main conductive area 103. The conductive material is electro-plated only over the main conductive area 103 until the thickness of the electro-plated conductive material corresponds to the maximum height of the insulation ridge 207. Since then, electro-plating is continued such that additionally electro-plated conductive material extends out onto the surface of the insulation ridge 207 as a sort of meniscus 409, the radius of which increases with increasing electro-plating time.

Figure 5:
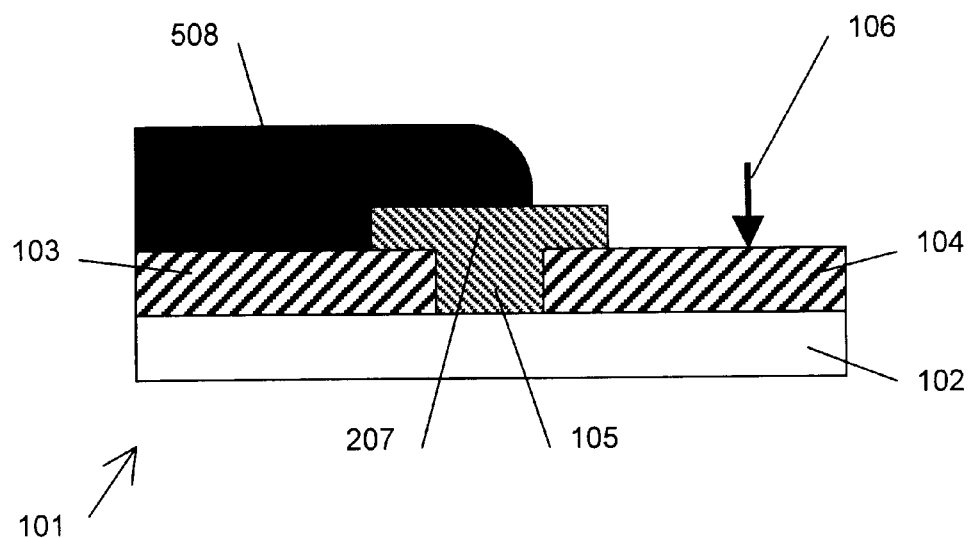
FIG. 5 shows a schematic side view of the second embodiment of the invention in a third mode.

FIG. 5 shows a schematic side view of the mandrel 101 from FIG. 4 with a third mode layer of conductive material 508. Between FIG. 4 and FIG. 5 electro-plating was continued, whereby the thickness of the electro-plated conductive material over the main conductive area 103 as well as the size of the meniscus 409 was further increased.

Figure 6:
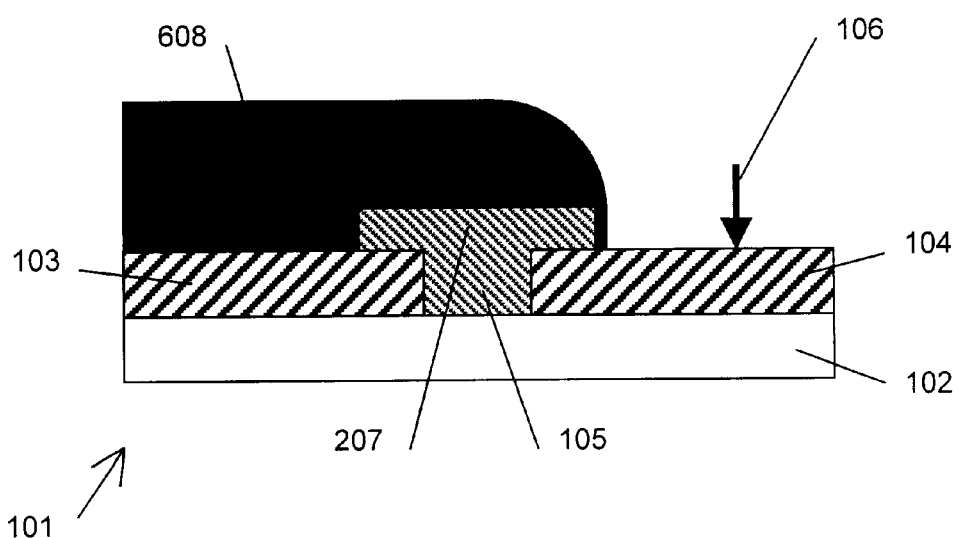
FIG. 6 shows a schematic side view of the second embodiment of the invention in a fourth mode.

In FIG. 6 electro-plating is preceded such that the electro-plated conductive material forms a fourth mode layer of conductive material 608, which finally extends to and contacts the insulated conductive area 104. At this point, an electrical contact between the main conductive area 103 and the insulated conductive area 104 is established through the electro-plated layer of conductive material. Due to the fact, that for electro-plating the main conductive area 103 has to be charged, the electrical contact between the main conductive area 103 and the insulated conductive area 104 leads to a charging of the insulated conductive area 104. The sensor 106 finally detects the start-up time, when the electro-plated conductive material establishes an electrical contact between the charged main conductive area 103 and the insulated conductive area 104. Connected to the sensor 106 is an electronic circuit for controlling the electro-plating process, which stops the electro-plating process as soon as the insulated conductive area 104 is charged.

Figure 7:
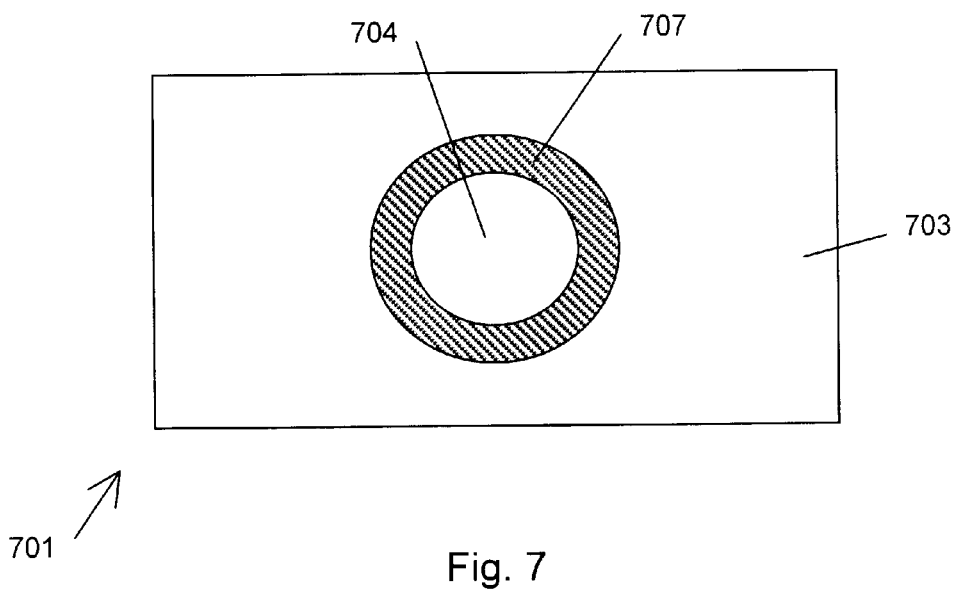
FIG. 7 shows a schematic top view of a third embodiment of the invention.

FIG. 7 shows a schematic top view of a mandrel 701 according to a third embodiment of the invention. Here, the insulated conductive area 704 is formed as a circular plane. Therefore, the insulation region 707 is formed as a closed ring around the insulated conductive area 704 to completely insulate the insulated conductive area 704 from the main conductive area 703.

Figure 8:
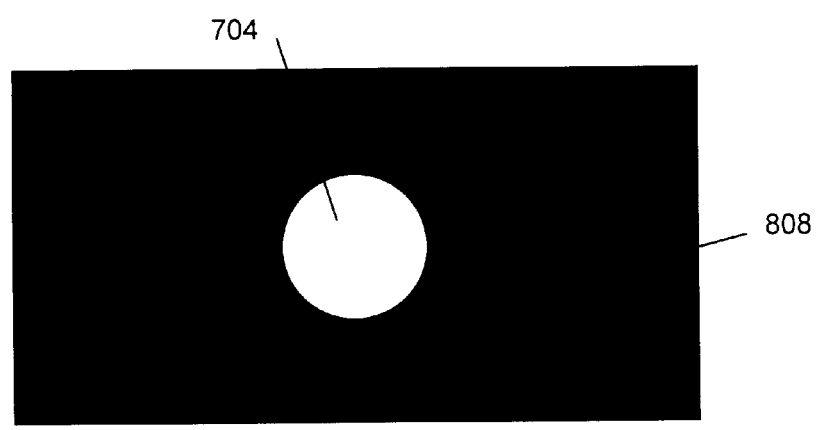
FIG. 8 shows a schematic top view of the third embodiment of the invention in the fourth mode as described in FIG. 6.

FIG. 8 shows a schematic top view of the mandrel 701 according to the third embodiment of the invention as described in FIG. 7 with a fourth mode layer of conductive material 808, which was electro-plated over the main conductive area 703 as described in FIG. 6. Removing the electro-plated conductive material from the mandrel 701 yields a sheet of conductive material with a bore somewhere in the sheet. In case of patterning the initial conductive layer with the desired insulated conductive areas 704 this yields an orifice sheet. The final orifice sheet is now available with a desired number and shape of bores at desired positions in the final orifice sheet by forming the shape of the insulation region 707 using epitaxial growth and chemical etch in a desired manner.

What is claimed is:

1. A device for detecting an end point of electro-plating, comprising:
    a mandrel having a substrate and a patterned conductive layer with a main conductive area and an insulated conductive area being insulated from the main conductive area on the substrate, an insulation region interposed between the main conductive area and the insulated conductive area, and
    a sensor electrically connected to the insulated conductive area for detecting a signal which indicates the end point of electro-plating.
2. A device according to claim 1, wherein the insulated conductive area on the mandrel is a circular plane.
3. A device according to claim 1, wherein the main conductive area is charged.
4. A device according to claim 1, wherein conductive material is electro-plated on the main conductive area.
5. A device according to claim 4, wherein nickel is used as conductive material, which is electra-plated on the main conductive area.
6. A device according to claim 1,
    wherein the insulated conductive area is designed to be charged by electra-plating a layer of conductive material crossing into the insulation region such that an electrical contact is established between the insulated conductive area and the main conductive area,
    where the sensor is used for detecting start-up time of charging of the insulated conductive area.
7. A device according to claim 1, wherein the substrate comprises silicon.
8. A device according to claim 1, wherein the main conductive area as well as the insulated conductive area comprise a chromium steel alloy.
9. A device according to claim 8, wherein the chromium steel alloy comprises between 16% and 18% chromium.
10. A device according to claim 1, wherein the insulation region comprises an insulation trench.
11. A device according to claim 10, wherein the insulation trench is filled with insulating material, which comprises silicon carbide.
12. A method of detecting an end point of electro-plating, comprising:
    providing a mandrel having a conductive layer on a substrate,
    providing an insulation region interposed on the substrate between two areas of the conductive layer such that the conductive layer is divided into a main conductive area and an insulated conductive area being insulated from the main conductive area,
    electrically connecting a sensor to the insulated conductive area,
    electra-plating a layer of conductive material on the main conductive area to cross into the insulation region, and
    detecting a signal which indicates the end point of electra-plating through the sensor when the electra-plated layer of conductive material contacts the insulated conductive area.
13. A method according to claim 12,
    wherein the insulated conductive area is charged by the electro-plated layer of conductive material contacting the insulated conductive area, thereby establishing an electrical contact between the insulated conductive area and the main conductive area, and
    wherein the sensor detects start-up time of charging of the insulated conductive area.
14. A method according to claim 12, wherein the insulation region is provided by etching an insulation trench in the conductive layer up to the substrate.
15. A method according to claim 14, wherein the insulation trench is filled with insulating material.
16. A method according to claim 12, wherein the insulation region is provided by forming an insulation ridge on the substrate first, and forming the conductive layer on the substrate afterwards, yielding the main conductive area and the insulated conductive area already separated by the insulation ridge.
17. A method according to claim 12, wherein the insulated conductive area is provided as a circular plane exposing an inner circular area, which is not electro-plated, thereby forming an electro-plated layer of conductive material with an orifice.
18. A method of providing an orifice sheet, wherein the electro-plated layer of conductive material with the orifice according to claim 17 is peeled off the mandrel, thereby yielding the orifice sheet.

* * * * *